US008861686B2

(12) United States Patent
Kim

(10) Patent No.: US 8,861,686 B2
(45) Date of Patent: Oct. 14, 2014

(54) X-RAY GENERATING APPARATUS AND X-RAY IMAGING SYSTEM HAVING THE SAME

(75) Inventor: Ki Yeo Kim, Gyeonggi-do (KR)

(73) Assignee: Samsung Electronics Co., Ltd., Yeongtong-gu, Suwon-si, Gyeonggi-do (KR)

(*) Notice: Subject to any disclaimer, the term of this patent is extended or adjusted under 35 U.S.C. 154(b) by 109 days.

(21) Appl. No.: 13/366,654

(22) Filed: Feb. 6, 2012

(65) Prior Publication Data
US 2012/0201353 A1 Aug. 9, 2012

(30) Foreign Application Priority Data
Feb. 9, 2011 (KR) ........................ 10-2011-0011452

(51) Int. Cl.
*G21K 1/00* (2006.01)
(52) U.S. Cl.
USPC .......................................... 378/154; 378/149
(58) Field of Classification Search
USPC .................... 378/122, 145–153, 154
See application file for complete search history.

(56) References Cited

U.S. PATENT DOCUMENTS

| 6,333,968 B1* | 12/2001 | Whitlock et al. ............. 378/136 |
| 2003/0128811 A1* | 7/2003 | Verman et al. .................. 378/84 |
| 2005/0105690 A1 | 5/2005 | Pau et al. |
| 2011/0206187 A1* | 8/2011 | Lee et al. ...................... 378/122 |

FOREIGN PATENT DOCUMENTS

| JP | 02-256285 A | 10/1990 |
| KR | 10-2003-0041851 A | 5/2003 |

* cited by examiner

*Primary Examiner* — Hoon Song
(74) *Attorney, Agent, or Firm* — Cha & Reiter, LLC

(57) ABSTRACT

An X-ray imaging system that generates a large amount of X-rays sufficient for X-ray imaging and collimates X-rays in a direction parallel to each other at high density. The X-ray imaging system includes an X-ray generating apparatus to generate and emit X-rays, a detector to detect the X-rays emitted from the X-ray generating apparatus, and at least one collimator disposed between the X-ray generating apparatus and the detector to prevent dispersion of the X-rays emitted from the X-ray generating apparatus.

22 Claims, 8 Drawing Sheets

X-RAY GENERATING APPARATUS AND X-RAY IMAGING SYSTEM HAVING THE SAME

CLAIM OF PRIORITY

This application claims the benefit of the earlier filing date Korean Patent Application No. 2011-0011452, filed on Feb. 9, 2011 in the Korean Intellectual Property Office, the entire disclosure of which is incorporated herein by reference.

BACKGROUND OF THE INVENTION

1. Field of the Invention

The present invention relates to an X-ray generating apparatus used in non-destructive X-ray imaging and diagnosis and an X-ray imaging system having the same.

2. Description of the Related Art

An X-ray generating apparatus is widely used in medical diagnosis and non-destructive testing to generate images of various structures, which images may be used to detect defects in the structures.

Generally, a medical X-ray generating apparatus has a structure in which thermal electrons are emitted from a cathode filament which is heated to high temperature, and then the emitted electrons are accelerated so as to collide with a rotating anode target to, to thereby generate X-rays.

In such a structure in which thermal electrons collide with the rotating anode target, a large amount of X-rays are generated. However, with such apparatus, several peripheral devices are needed, such as, to heat the cathode filament, a rotating device to rotate the anode, and a cooling device may be needed, with the combined result that the volume and weight of the X-ray generating apparatus is substantially increased. Most of the thermal electrons emitted from the cathode filament are converted into heat, and remaining the thermal electrons are used to generate X-rays. For this reason, X-ray generating apparatus are generally inefficient and exhibit low resolution.

In recent years, research has been conducted into a field emission display (FED) type X-ray generating apparatus (hereinafter, referred to as a flat plate type X-ray generating apparatus). The flat X-ray generating apparatus has a structure in which needle-shaped emitters each having a size of about several tens of a nanometer (nm) are disposed on a flat plate, and a high electric field is applied to the emitters so that electrons emitted from the emitters are forced to collide with an anode target so as to generate X-rays.

In the flat plate type X-ray generating apparatus, the size of the apparatus is small, and X-ray generation is efficiently controlled. However, it is difficult to generate an amount of X-rays that are sufficiently collimated for X-ray imaging. In particular, it is difficult to collimate X-rays in a direction in parallel to each other (that is, in a plurality of parallel paths). For this reason, the flat plate type X-ray generating apparatus is not widely used for medical purposes.

SUMMARY OF THE INVENTION

It is an aspect of the present invention to provide an X-ray generating apparatus having a structure to generate a large amount of X-rays sufficient for X-ray imaging and an X-ray imaging system including the same.

It is another aspect of the present invention to provide an X-ray generating apparatus that collimates X-rays in a direction parallel to each other at high density and an X-ray imaging system including the same.

It is another aspect of the present invention to provide an X-ray generating apparatus that individually controls emitters placed on a flat plate to uniformly generate X-rays and an X-ray imaging system including the same.

It is yet another aspect of the present invention to provide an X-ray imaging system that collimates X-rays emitted from an X-ray generating apparatus in a direction parallel to each other.

Additional aspects of the invention will be set forth in part in the description which follows and, in part, will be obvious from the description, or may be learned by practice of the invention.

In accordance with an aspect of the present invention, an X-ray imaging system includes an X-ray generating apparatus to generate and emit X-rays, a detector to detect the X-rays emitted from the X-ray generating apparatus, and at least one collimator disposed between the X-ray generating apparatus and the detector, the collimator having a collimation axis in parallel to the advancing direction of the X-rays emitted by the X-ray generating apparatus so as to prevent dispersion of the X-rays emitted from the X-ray generating apparatus.

The collimator may include a plurality of capillary tubes having their collimation axes disposed in parallel to each other, and each of the capillary tubes may have at least one diffraction layer to diffract X-rays passing therethrough.

The diffraction layer may include at least one selected from a group of tungsten (W), molybdenum (Mo), lead (Pb) and platinum (Pt).

Each of the capillary tubes may include at least one transmission layer to transmit the X-rays diffracted by the diffraction layer, and the diffraction layer and the transmission layer may be alternately disposed from the outside of each of the capillary tubes toward the center of each of the capillary tubes to form a layered structure thereby.

The transmission layer may include at least one selected from among carbon (C), silicon (Si), aluminum (Al), polymer, nitride and oxide.

The collimator may include a plurality of crystal lattices to filter X-rays having a specific wavelength.

The X-ray generating apparatus may include a cathode unit having a plurality of emitters to emit electrons and gates to form an electric field between the gates and the emitters so that electrons are emitted from the emitters, and an anode unit having a target with which the electrons emitted from the cathode unit collide to generate X-rays.

The cathode unit may be formed in a flat shape, and the emitters may be disposed at the surface of the flat cathode unit in a matrix.

The target may be formed in a rugged shape to prevent dispersion of X-rays.

The target may have at least one diffraction layer to diffract X-rays.

The diffraction layer may include at least one selected from a group of tungsten (W), molybdenum (Mo), lead (Pb) and platinum (Pt).

The target may include at least one transmission layer to transmit the X-rays diffracted by the diffraction layer, and the diffraction layer and the transmission layer may be alternately disposed to form a rugged layered structure.

The transmission layer may include at least one selected from among carbon (C), silicon (Si), aluminum (Al), polymer, nitride and oxide.

The emitters may be individually controllable.

The collimator may be disposed in parallel to the X-ray generating apparatus, and the collimator or the X-ray generating apparatus may be disposed so as to be movable in a direction parallel to each other.

In accordance with another aspect of the present invention, an X-ray generating apparatus includes a flat cathode unit, emitters disposed at a surface of the cathode unit in a matrix, gates disposed respectively between the emitters so that electrons are emitted from the emitters, an anode unit to form an electric field between the anode unit and the cathode unit to accelerate the electrons emitted from the emitters, a target with which the electrons emitted from the emitters collide to generate X-rays, and a rugged portion to collimate X-rays in a direction parallel to a direction in which the electrons emitted from the emitters are accelerated.

The rugged portion may have at least one diffraction layer to diffract X-rays.

The diffraction layer may include at least one selected from a group of tungsten (W), molybdenum (Mo), lead (Pb) and platinum (Pt).

The target may include at least one transmission layer to transmit the X-rays diffracted by the diffraction layer, and the diffraction layer and the transmission layer may be alternately disposed to form a rugged layered structure.

The transmission layer may include at least one selected from a group of carbon (C), silicon (Si), aluminum (Al), polymer, nitride and oxide.

The emitters may be individually controllable.

The X-rays may be transmitted through the anode unit and may be emitted from the X-ray generating apparatus.

The X-rays may be transmitted through the cathode unit and may be emitted from the X-ray generating apparatus.

In accordance with another aspect of the present invention, an X-ray generating apparatus includes a plurality of electron generating elements disposed on a two-dimensional flat plate and a target, disposed opposite to the electron generating elements, with which electrons emitted from the electron generating elements collide to generate X-rays, wherein the target includes at least one rugged diffraction layer to diffract X-rays and at least one transmission layer coupled to a rear of the diffraction layer to transmit the X-rays diffracted by the diffraction layer.

The diffraction layer and the transmission layer may be alternately disposed.

The diffraction layer may include at least one selected from among tungsten (W), molybdenum (Mo), lead (Pb) and platinum (Pt).

The transmission layer may include at least one selected from among carbon (C), silicon (Si), aluminum (Al), polymer, nitride and oxide.

The electron generating elements may be individually controllable.

Distances between the diffraction layers may be equal to each other.

In accordance with yet another aspect of the present invention, an X-ray imaging system includes an X-ray generating apparatus to generate X-rays, a detector to detect the X-rays emitted from the X-ray generating apparatus in an advancing direction so as to be transmitted through a subject to be tested, and at least one collimator to collimate the X-rays emitted from the X-ray generating apparatus, wherein the collimator is disposed between the X-ray generating apparatus and the subject or between the subject and the detector, and having a collimation axis oriented so as to collimate X-rays traveling in the advancing direction.

The collimator may include a plurality of capillary tubes each having a longitudinal axis disposed in parallel to each other and the advancing direction, and each of the capillary tubes may include at least one diffraction layer to diffract X-rays passing therethrough and at least one transmission layer to transmit the X-rays diffracted by the diffraction layer, the diffraction layer and the transmission layer being alternately disposed from the outside of each of the capillary tubes toward the center of each of the capillary tubes to form a layered structure.

The diffraction layer and the transmission layer may be alternately disposed, and distances between the diffraction layers may be equal to each other.

The collimator may include a plurality of crystal lattices to filter X-rays traveling in the advancing direction which have a specific wavelength.

The collimator is oriented so its collimation axis may be disposed in parallel to the advancing direction of the X-rays emitted by X-ray generating apparatus, and the collimator or the X-ray generating apparatus may be disposed so as to be movable in a direction parallel to each other.

The X-ray generating apparatus may include a cathode unit having a plurality of emitters to emit electrons and gates to form an electric field between the gates and the emitters so that electrons are emitted from the emitters and an anode unit having a target with which the electrons emitted from the cathode unit collide to generate X-rays.

The target may include a plurality of layers made of different materials.

The layers may include at least one diffraction layer to diffract X-rays and at least one transmission layer to transmit X-rays, and the diffraction layer and the transmission layer may be alternately disposed to form a rugged layered structure.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION OF THE INVENTION

Figure 1:
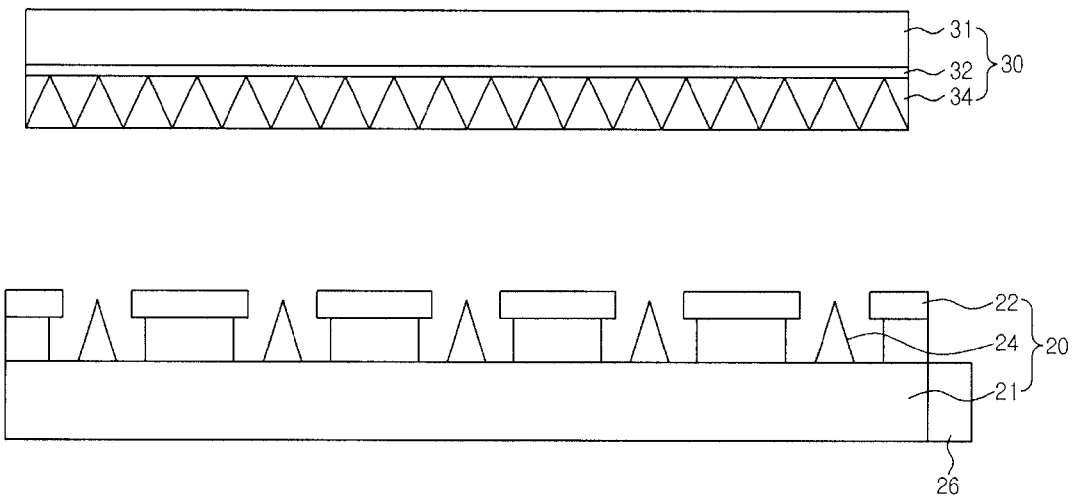
FIG. 1 is a view showing the principal construction of an X-ray generating apparatus according to an embodiment of the present invention.

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

Reference will now be made in detail to the embodiments of the present invention, examples of which are illustrated in the accompanying drawings, wherein like reference numerals refer to like elements throughout.

FIG. 1 is a view showing the principal construction of an X-ray generating apparatus according to an embodiment of the present invention.

As shown in FIG. 1, the X-ray generating apparatus 10 includes a cathode unit 20 having a plurality of emitters 22 to emit electrons and a plurality of gates 24 to apply a strong electric field to the respective emitters 22 so that electrons are emitted from the emitters and an anode unit 30 having a target 34 with which the electrons emitted from the cathode unit 20 collide to generate X-rays.

The cathode unit 20 has a flat cathode substrate 21, a plurality of emitters 22 disposed at the surface of the cathode substrate 21 in a matrix, gates 24 disposed respectively between the emitters 22 to apply an electric field to the emitters 22 so that electrons are emitted from the emitters 22, and an electronic controller 26 to individually control the emitters 22.

The cathode substrate 21 is made of glass or silicon exhibiting high electrical insulation.

A Spindt type electron generating element may be used as each of the emitters 22. The Spindt type electron generating element is formed in a conical shape. The tip of the Spindt type electron generating element has a diameter of about several tens of nm. Alternatively, a carbon nanotube type electron generating element having a micro-structure of several tens of nm may be used as each of the emitters 22. When voltage of several tens to several hundreds of V is applied to the Spindt type or carbon nanotube type electron generating element, electrons are emitted from the tip of the electron generating element according to an electric field emission phenomenon.

In addition to the Spindt type and carbon nanotube type electron generating elements, various electron generating elements may be used as the emitters 22. For example, a metal insulator metal (MTM) type element and metal insulator semiconductor (MIS) type element may be used. Furthermore, all cold cathode type electron generating elements, such as a semiconductor PN junction type element, a Schottky junction type element and a carbon-based thin film element made of nano carbon fiber, may be used.

The electronic controller 26 may individually control the amount of electrons emitted from the emitters 22 using, for example, a matrix type signal to establish an on/off control of the amount of electrons emitted from the emitters 22.

The X-ray generating apparatus 10, using the cold cathode type electron generating elements as the emitters 22, supplies voltage to the electron generating elements at room temperature without heating the cathode unit 20 to emit electrons. Consequently, waiting time for X-ray generation may not be needed. Also, power to heat the cathode unit 20 may not be needed, thereby emitting X-rays more efficiently as compared with a heated cathode method. Since the respective emitters 22 are turned on/off by the electronic controller 26, the emitters 22 may be selectively driven, and high-speed response may be achieved.

The anode unit 30 has a flat anode substrate 31, an anode 32 maintained at high voltage and a target 34 with which electrons emitted from the cathode unit 20 collide.

The anode substrate 31 is formed in a shape corresponding to the cathode substrate 21. In the same manner as the cathode substrate 21, the anode substrate 31 is made of glass or silicon exhibiting high electrical insulation.

The anode 32, to which high voltage is applied, causes electrons emitted from the emitters 22 to accelerate so that the electrons collide with the target 34.

Figure 2:
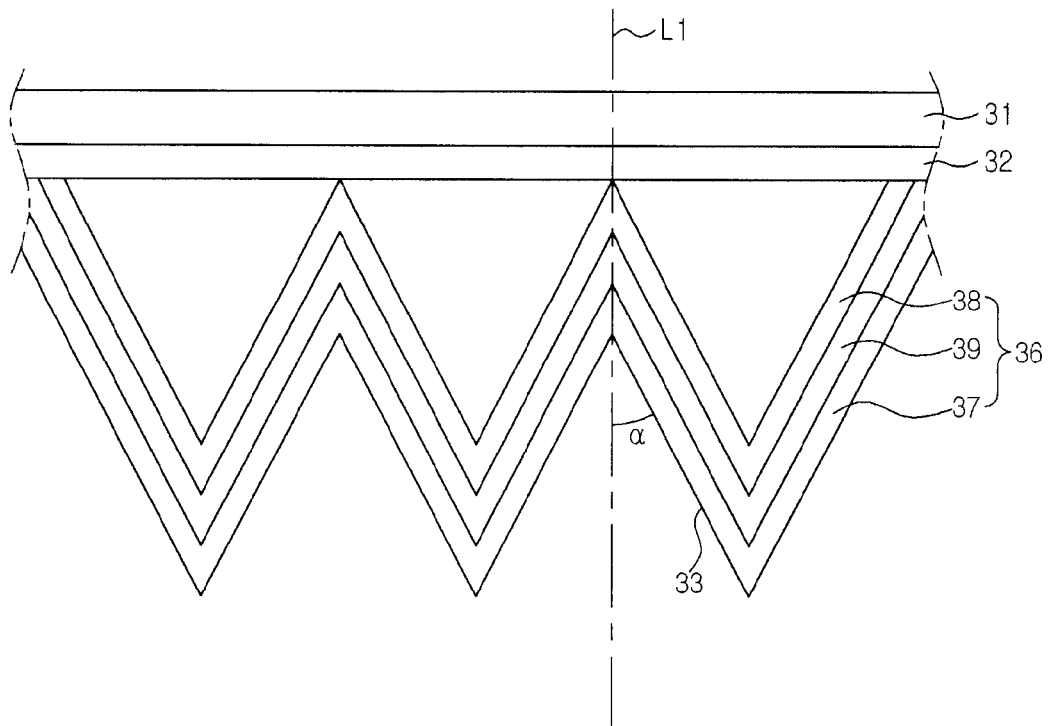
FIG. 2 is an enlarged view of a target shown in FIG. 1.

FIG. 2 is an enlarged view of the target shown in FIG. 1.

As shown in FIGS. 1 and 2, the target 34 is formed in a micro conical or pyramidal rugged shape. Since the target 34 is formed in the rugged shape, effective collision area of the target 34 with which electrons emitted from the emitters 22 collide is increased (because they pass through target 34 diagonally rather than in a manner perpendicular thereto), thereby increasing the amount of X-rays generated and thus improving cooling efficiency of the anode unit 30.

An angle α between a rugged surface 33 and a straight line L perpendicular to the anode unit 30 or the cathode unit 20 may be substantially anywhere from 0.1 to 2 degrees, in order to obtain X-rays advancing in a direction substantially perpendicular to the anode unit 30 or the cathode unit 20 of FIG. 1.

Also, the rugged target 34 has a plurality of alternately disposed layers 36. The layers 36 include a generation layer 37 to generate X-rays, a diffraction layer 39 to diffract the generated X-rays and a transmission layer to transmit the diffracted X-rays.

The generation layer 37 is located at the outermost layer of the target 34, i.e. a portion with which electrons initially collide. The generation layer 37 is made of an element, the atomic number of which is sufficiently large to easily generate X-rays upon the initial collision. The generation layer 37 may be made of tungsten (W) or molybdenum (Mo).

The diffraction layer 38 is coupled to the rear of the generation layer 37 to diffract X-rays generated from the generation layer 37. The diffraction layer 38 is made of an element, the atomic number of which is sufficiently large to diffract or reflect X-rays in a specific direction based on an incidence direction of the X-rays. The diffraction layer 38 may be made of tungsten (W), molybdenum (Mo), lead (Pb) or platinum (Pt).

The transmission layer 39 is coupled to the front of the diffraction layer 38 to transmit X-rays diffracted by the diffraction layer 38. The transmission layer 39 is made of an element, the atomic number of which is sufficiently small not to reflect or absorb X-rays. The transmission layer 39 may be made of carbon (C), silicon (Si) or aluminum (Al). Alternatively, the transmission layer 39 may be made of polymer, nitride or oxide.

At the rear of the transmission layer 39 may be alternately disposed another diffraction layer 38 and transmission layer 39. The transmission layer 39 is disposed between the diffraction layers 38 to diffract X-rays passing between the generation layer 37 and the diffraction layer 38 or between the diffraction layers 38

Since the target 34 is formed to have a rugged layered structure in which the diffraction layers 38 and the transmission layers 39 are alternately disposed, X-rays the are transmitted therefrom are collimated in a direction perpendicular to the flat anode unit 30 or cathode unit 20.

The target 34 collimates X-rays so that the X-rays although they are not completely perpendicular to the plane of the anode unit 30 or cathode unit 20, they are approximately perpendicular to the plane of the anode unit 30 or cathode unit 20.

Figure 3:
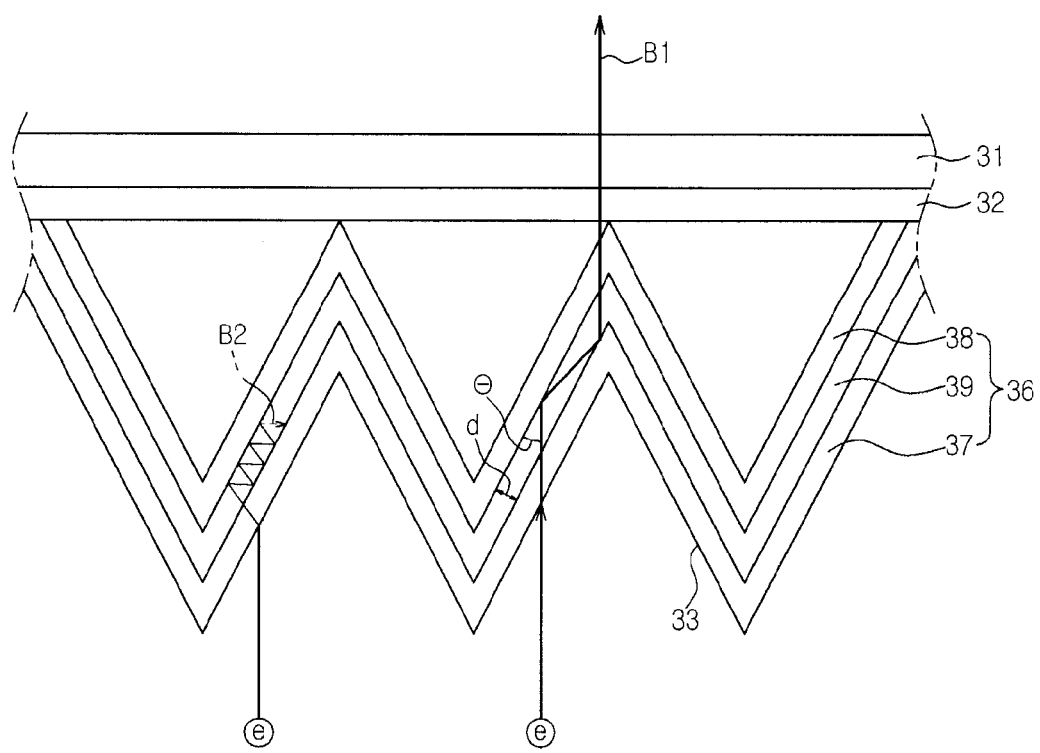
FIG. 3 is a view showing a principle by which X-rays generated through the target shown in FIG. 2 are collimated in a direction perpendicular to an anode unit or a cathode unit.

FIG. 3 is a view showing a principle by which X-rays generated through the target shown in FIG. 2 are collimated in a direction perpendicular to the anode unit or the cathode unit.

As shown in FIG. 3, X-rays generated from accelerated electrons colliding with the generation layer 37 pass through the diffraction layer 38 and the transmission layer 39, alternately disposed at the rear of the generation layer 37, with the result that they are collimated in a direction approximately perpendicular to the flat anode unit 30 or cathode unit 20.

The X-rays generated from the generation layer 37 do not have a predetermined or consistently regular directivity and are thus emitted in all directions. During emission of the X-rays in all directions, some of the X-rays are diffracted while passing through the transmission layer 39 between the generation layer 37 and the diffraction layer 38 or between the diffraction layers 38, advance in a specific direction, are reflected one or more times as the result of collision with the diffraction layer 38, and gradually result to advance in a direction approximately perpendicular to the flat anode unit 30 or cathode unit 20.

As previously described, the rugged surface 33 is almost parallel to the straight line L1 perpendicular to the anode unit 30 or cathode unit 20. Consequently, an X-ray B1 emitted in a direction approximately parallel to the rugged surface 33, among X-rays generated from the generation layer 37, is repeatedly diffracted, reflected and transmitted. As a result, the X-ray B1 advances in a direction substantially perpendicular to the anode unit 30 or cathode unit 20 and is emitted from the X-ray generating apparatus 10 via the anode substrate 31 and the anode 32. On the other hand, an X-ray B2 forming an angle of predetermined degrees or more with the rugged surface 33, among X-rays generated from the generation layer 37, is reflected many times by collision between the diffraction layers 38 with the result that the X-ray B2 abruptly loses energy. Consequently, the X-ray B2 is not emitted from the X-ray generating apparatus 10 but is absorbed. In this way, the target 34 is formed to have a rugged layered structure, thereby effectively achieving collimation of X-rays in a direction approximately perpendicular to the anode unit 30 or cathode unit 20.

Also, in accordance with another embodiment of the invention, a diffraction phenomenon is used during collimation of X-rays to collimate X-rays having a specific wavelength.

The diffraction phenomenon of X-rays is based on Bragg's law.

$n*\lambda = 2*d*\sin\theta$ (n is an integer, $\lambda$ is the wavelength of an X-ray, d is the distance between diffraction layers, and $\theta$ is an angle between the incident X-ray and a diffraction layer).

If $\theta$ is increased, the angle between the X-ray and the diffraction layer 38 is increased with the result that the X-ray is not diffracted but reflected. For this reason, $\theta$ is limited to a predetermined range or less, and the distance d between the diffraction layers 39 is fixed to a certain value with the result that the wavelength $\lambda$ of the diffracted X-ray is specified by values of $\theta$ and d. Consequently, the distance d between the diffraction layers 38 may be adjusted to collimate only X-rays having wavelengths that fall within a desired band of wavelengths. In this case, it may be necessary to uniformly and equally maintain the distance d between the diffraction layers 38 to prevent the occurrence of an extinction interference phenomenon. When X-rays having a specific wavelength are used, precise image information regarding a subject may be obtained.

Figure 4:
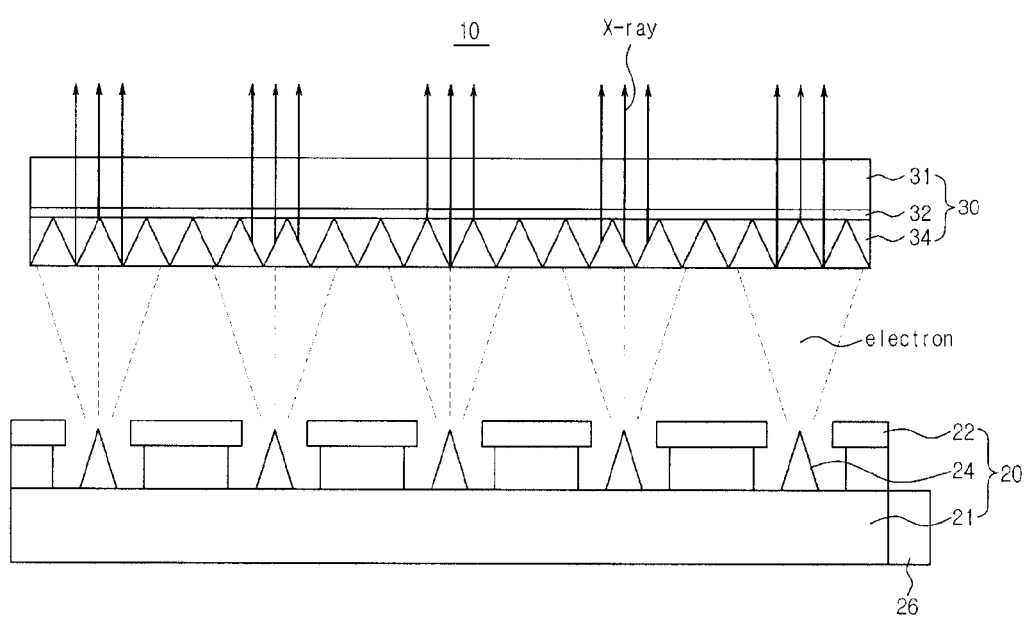
FIG. 4 is a view showing X-rays transmitted through the anode unit of the X-ray generating apparatus and emitted from the X-ray generating apparatus.
Figure 5:
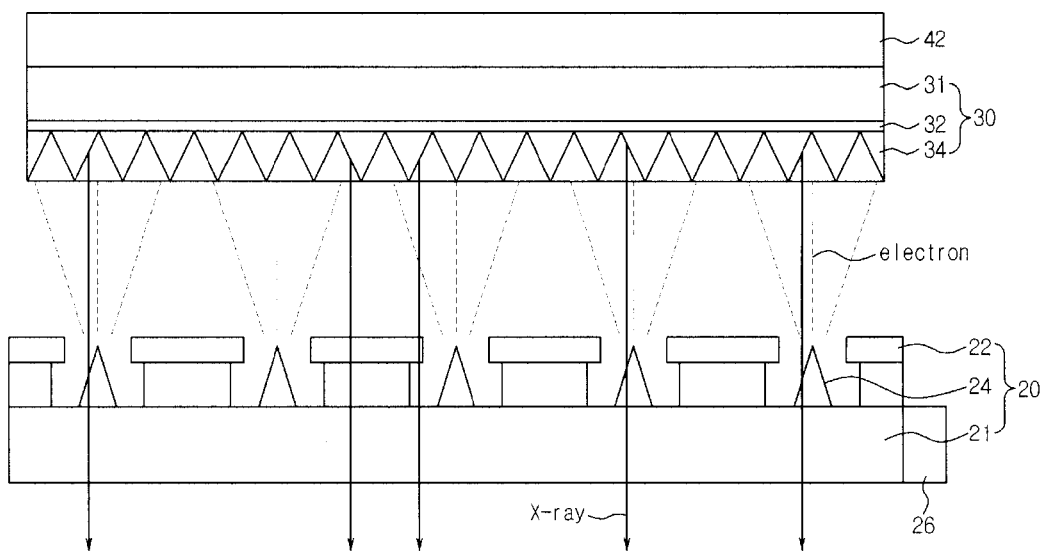
FIG. 5 is a view showing X-rays transmitted through the cathode unit of the X-ray generating apparatus and emitted from the X-ray generating apparatus.

FIG. 4 is a view showing X-rays transmitted through the anode unit of the X-ray generating apparatus and emitted from the X-ray generating apparatus, and FIG. 5 is a view showing X-rays transmitted through the cathode unit of the X-ray generating apparatus and emitted from the X-ray generating apparatus.

The X-ray generating apparatus may use X-rays transmitted through the anode unit 30 or through the cathode unit 20.

When X-rays transmitted through the anode unit 30 are used, as shown in FIG. 4, electrons emitted from the emitters 22 are accelerated by the anode 32 and collide with the generation layer 37 of the target 34. X-rays generated when the electrons collide with the generation layer 37 pass through the diffraction layer 38 and the transmission layer 39, constituting a rugged layered structure, advance in a direction in which the X-rays are transmitted through the target 34 (a direction perpendicular to the anode unit 30 or cathode unit 20), are sequentially transmitted through the target 34, the anode 32 and the anode substrate 31, and are emitted from the X-ray generating apparatus 10.

The anode 32 and the anode substrate 31 are formed of a material, such as glass or silicon, which transmits X-rays satisfactorily, that is, without significant reflection or absorption.

When X-rays transmitted through the cathode unit 20 are used, as shown in FIG. 5, electrons emitted from the emitters 22 are accelerated by the anode 32 and collide with the generation layer 37 of the target 34. X-rays generated at this time pass through the diffraction layer 38 and the transmission layer 39, constituting a rugged layered structure, or are reflected from the diffraction layer 38, advance in a direction in which the X-rays are reflected from the target 34 (a direction perpendicular to the anode unit 30 or cathode unit 20), are transmitted through the cathode unit 20, and are emitted from the X-ray generating apparatus 10.

The cathode substrate 21 is formed of a material, such as glass or silicon, which transmits X-rays satisfactorily.

When X-rays transmitted through the cathode unit 20 are used as described above, a cooling device 42 used to cool the anode 32 may be coupled to the rear of the anode unit 30 without limitation, and the thickness of the anode 32, which is connected with electron acceleration performance, may be increased.

Hereinafter, an X-ray imaging system 100 including the X-ray generating apparatus 10 according to the embodiment of the present invention will be described in detail.

Figure 6:
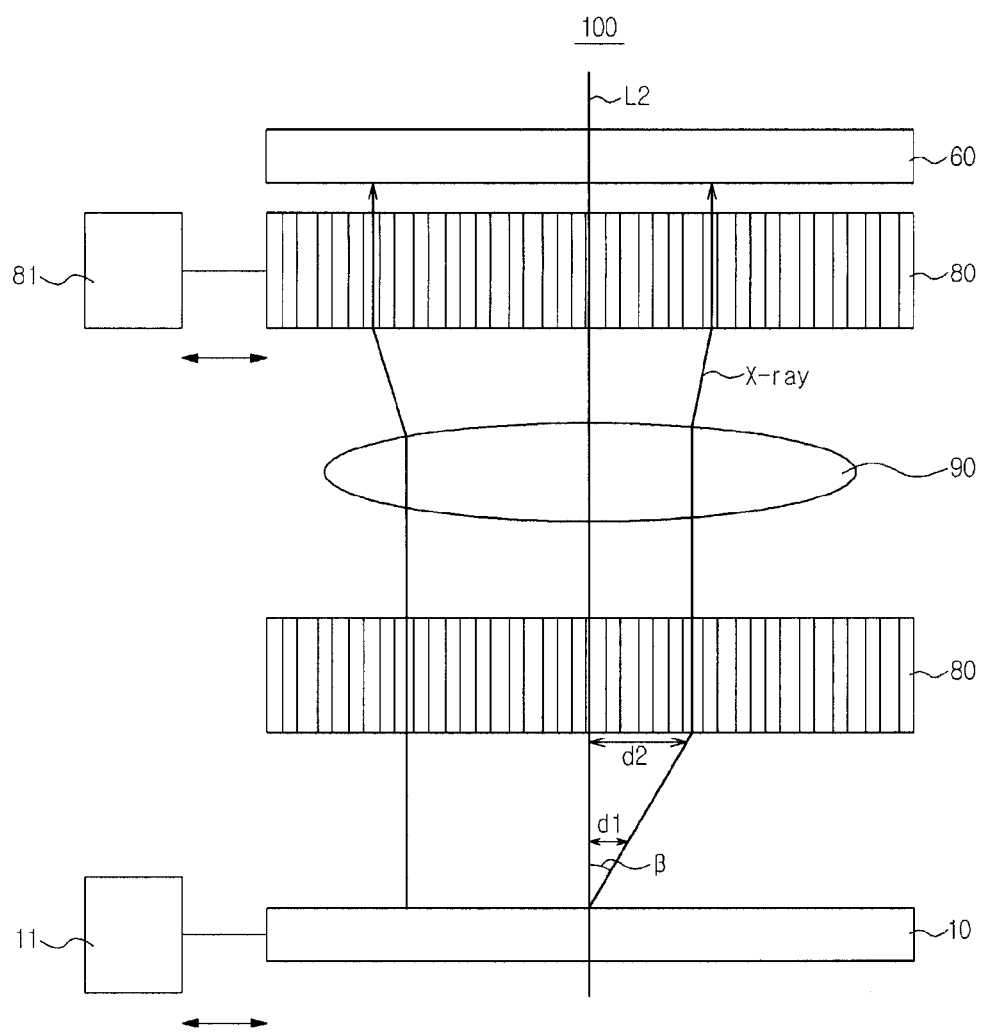
FIG. 6 is a view showing the principal construction of an X-ray imaging system according to an embodiment of the present invention.

FIG. 6 is a view showing the principal construction of an X-ray imaging system according to an embodiment of the present invention.

As shown in FIG. 6, the X-ray imaging system includes an X-ray generating apparatus 10 to generate and emit X-rays, a detector 60 to detect the X-rays emitted from the X-ray generating apparatus 10 and a collimator 80 disposed between the X-ray generating apparatus 10 and the detector 60 to prevent dispersion of the X-rays emitted from the X-ray generating apparatus 10.

The collimator 80 collimates (makes substantially parallel) the X-rays after they have been emitted from the X-ray generating apparatus 10 and before the X-rays are incident upon a subject or collimates the X-rays after they have passed through the subject 90 before the X-rays are incident upon the detector 60. The collimator 80 does not completely collimate X-rays, but it substantially reduces an emission angle of the X-rays with respect to an incidence angle of the X-rays so that the X-rays incident upon the subject 90 or the detector 60 are approximately perpendicular to the plane of the detector 60. The incidence angle and emission angle are inclinations to a direction perpendicular to the plane of the collimator 80 or the detector 60. It is also noted that the direction perpendicular to the plan of the collimator 80 is in fact the direction that the X-rays pass through the collimator with the least attenuation (the advancing direction of X-rays), and hereinafter this direction is called the Axial direction of the collimator. For example, reduction of incidence angle to the detector 60 means that X-rays incident upon the detector 60 become closer to a direction perpendicular to the plane of the detector 60.

The collimator 80 is located between the X-ray generating apparatus 10 and the detector 60. More specifically, at least one collimator 80 is disposed between either the X-ray generating apparatus 10 and the subject 90 or between the subject 90 and the detector 60.

As X-rays emitted from the X-ray generating apparatus 10 become distant from the X-ray generating apparatus 10, the resolution of the X-rays is reduced. That is, when an X-ray is emitted from the X-ray generating apparatus 10 while forming an angle β with a straight line L2 perpendicular to the X-ray generating apparatus 10, an initial distance d1 between the X-ray and the straight line L2 is small. As the X-ray becomes distant from the X-ray generating apparatus 10, however, a distance d2 between the X-ray and the straight line L2 is increased (that is, the X-ray advances from the generating apparatus 10 it diverges from the straight line L2), which leads to the reduction in resolution of any image which may be formed from these X-rays. This is equally applied to X-rays transmitted through the subject 90 and incident upon the detector 60. The collimator 80 is disposed between the X-ray generating apparatus 10 and the subject 90 or between the subject 90 and the detector 60 so that the axial direction of collimator 80 is parallel to the direction perpendicular to the X-ray generating apparatus 10 as well as parallel to the direction perpendicular to the detector 60, to thereby improve a degree of collimation of the advancing X-rays (thereby making them more parallel), and thereby substantially preventing the reduction in resolution.

Consequently, in another embodiment of the invention, a plurality of collimators 80 may be disposed between the X-ray generating apparatus 10 and the detector 60 to improve resolution. However, when the advancing X-rays pass through the collimators 80, some of the X-rays are absorbed by the collimators 80, as will be described below. Because of such absorption, the number of the collimators 80 to be used in a particular embodiment is restricted so as to ensure that a sufficient amount of X-rays used to irradiate the subject 90 are remaining so as to reach the detector 60 and obtain a full image of the subject 90 at a desired resolution. According to the purpose of use and desired amount of resolution, therefore, the number of the collimators 80 disposed between the X-ray generating apparatus 10 and the detector 60 may be adjusted.

Also, the axial direction of collimator 80 is disposed in parallel to a direction perpendicular to the X-ray generating apparatus 10, so that only advancing X-rays substantially perpendicular to X-ray generating apparatus 10 pass therethrough. The X-ray generating apparatus 10 and the collimator 80 may be connected to moving devices 11 and 81 to minutely move or shift the X-ray generating apparatus 10 and the collimator 80 in a direction parallel to each other.

When the collimator 80 and the X-ray generating apparatus 10 are fixed, an image is obtained with respect only to a characteristic portion of the subject 90. On the other hand, when the collimator 80 or the X-ray generating apparatus 10 are minutely moved or shifted in coordination with each other, for example so as to eventually move completely around subject 90 in a 360 degree manner, an image is obtained with respect to all portions of the subject 90.

Meanwhile, the collimator 80 includes a plurality of capillary tubes which each have a longitudinal axis disposed substantially in parallel to the advancing direction of X-rays.

Figure 7:
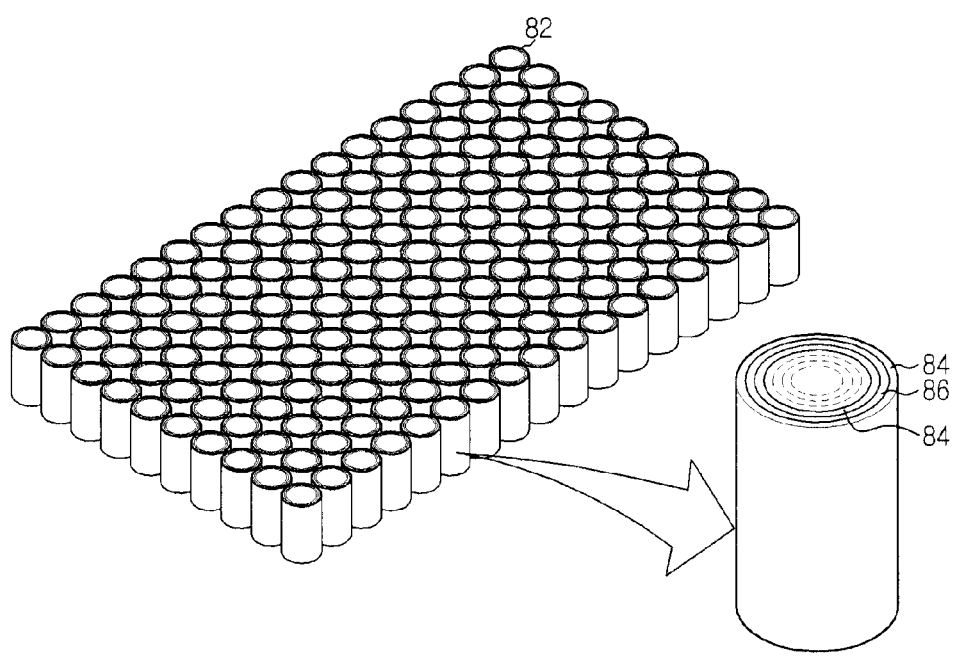
FIG. 7 is an enlarged view of capillary tubes constituting a collimator of FIG. 6.

FIG. 7 is an enlarged view of capillary tubes constituting the collimator of FIG. 6.

As shown in FIG. 7, a plurality of capillary tubes 82 is so that their longitudinal axes are arranged in parallel to each other. Each of the capillary tubes 82 includes at least one diffraction layer 84 to diffract X-rays passing therethrough and at least one transmission layer 86 to transmit X-rays. The diffraction layer 84 and the transmission layer 86 are alternately disposed from the outside of each of the capillary tubes 82 toward the center of each of the capillary tubes 82. That is, the diffraction layer 84 and the transmission layer 86 form a layered structure. The transmission layer 86 is disposed between the corresponding diffraction layers 84 to function as a path through which X-rays passing between the diffraction layers 84 are diffracted.

The diffraction layer 84 is made of an element, the atomic number of which is sufficiently large to diffract or reflect X-rays in a specific direction based on an incidence direction of the X-rays. The diffraction layer 84 may be made of tungsten (W), molybdenum (Mo), lead (Pb) or platinum (Pt). The transmission layer 86 is made of an element, the atomic number of which is sufficiently small not to reflect or absorb X-rays. The transmission layer 86 may be made of carbon (C), silicon (Si) or aluminum (Al). Alternatively, the transmission layer 86 may be made of polymer, nitride or oxide.

Each of the capillary tubes 82 is configured to have a layered structure in which the diffraction layers 84 and the transmission layer 86 are alternately disposed so that X-rays are collimated in a direction perpendicular to the plane of the X-ray generating apparatus 10 or the detector 60, that is, in parallel with the longitudinal axis of the capillary tubes 82.

Figure 8:
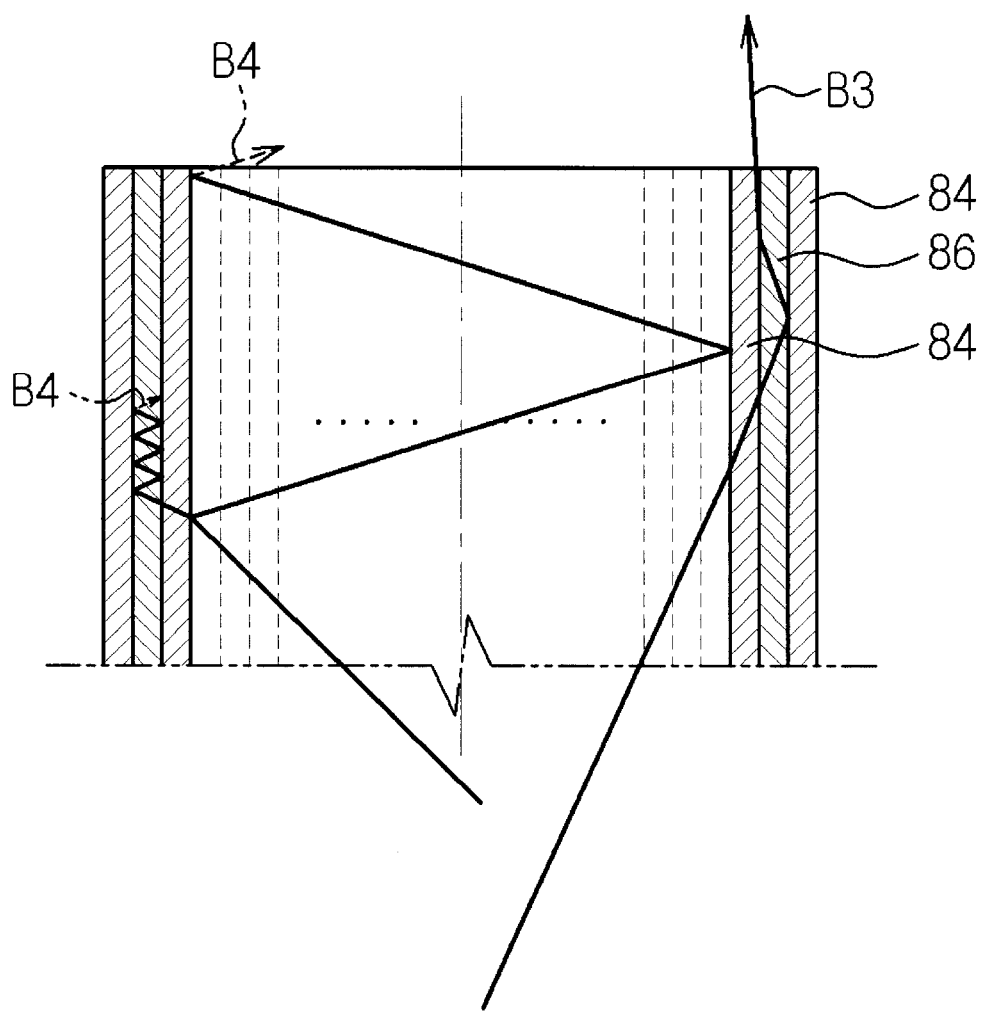
FIG. 8 is a view showing a principle by which X-rays are collimated while passing through one of the capillary tubes shown in FIG. 7.

FIG. 8 is a view showing a principle by which X-rays are collimated while passing through one of the capillary tubes shown in FIG. 7.

As shown in FIG. 8, X-rays incident upon a capillary tube 82 are collimated in a direction parallel to the longitudinal, axial, direction of the capillary tube 82 and are then emitted.

As previously described, the longitudinal axis of capillary tube 82 is substantially parallel to the straight line L2 perpendicular to the X-ray generating apparatus 10. Consequently, an X-ray B3 advancing in a direction approximately parallel to the longitudinal axis of capillary tube 82, among X-rays incident upon the capillary tube 82, is repeatedly diffracted, reflected and transmitted. This occurs because the angle between the incident X-ray and the diffraction layers 84 is less than a certain predetermined amount, such as previously explained for the angle θ described with respect to FIG. 3. As a result, the X-ray B3 advances in a direction substantially parallel to the longitudinal axis of the capillary tube 82 and is emitted from the collimator 80. On the other hand, an X-ray B4 forming an angle θ of predetermined degrees or more with the capillary tube 82, among X-rays incident upon the capillary tube 82, is reflected by collision between the diffraction layers 84 with the result that the X-ray B4 abruptly loses energy. Consequently, the X-ray B4 is not emitted from the collimator 80 but is absorbed. In this way, the collimator 80 is constituted by the capillary tubes 82 each having a layered structure to effectively collimate X-rays to be substantially parallel to the axial direction of collimator 80.

Also, a diffraction phenomenon is used during collimation of X-rays to collimate X-rays having a specific wavelength, the diffraction phenomenon of X-rays is based on Bragg's law as previously described, and therefore, a description thereof will be omitted.

The collimator 80 may include a plurality of crystal lattices instead of the capillary tubes 82. The crystal lattices filter and emit X-rays having a specific wavelength, thereby obtaining precise image information regarding a subject.

As is apparent from the above description, the X-ray imaging system generates a large amount of X-rays sufficient for X-ray imaging and collimates X-rays in a direction parallel to each other at high density, thereby improving resolution.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An X-ray imaging system comprising:
   an X-ray generating apparatus to generate and emit X-rays;
   a detector to detect the X-rays emitted from the X-ray generating apparatus; and
   at least one collimator disposed in a path between the X-ray generating apparatus and the detector to prevent dispersion of the X-rays emitted from the X-ray generating apparatus,
   wherein the collimator comprises a plurality of capillary tubes each having a longitudinal axis disposed in parallel to each other and an advancing direction of the x-rays, and
   each of the capillary tubes has at least one diffraction layer to diffract X-rays passing therethrough.

2. The X-ray imaging system according to claim 1, wherein the diffraction layer comprises at least one selected from the group of tungsten (W), molybdenum (Mo), lead (Pb) and platinum (Pt).

3. The X-ray imaging system according to claim 2, wherein each of the capillary tubes comprises at least one transmission layer to transmit the X-rays diffracted by the diffraction layer, and
   the diffraction layer and the transmission layer being alternately disposed from an outside of each of the capillary tubes toward a center of each of the capillary tubes, to form a layered structure thereby.

4. The X-ray imaging system according to claim 3, wherein the transmission layer comprises at least one selected from the group carbon (C), silicon (Si), aluminum (Al), polymer, nitride and oxide.

5. The X-ray imaging system according to claim 1, wherein the collimator comprises a plurality of crystal lattices to filter X-rays having a specific wavelength.

6. The X-ray imaging system according to claim 1, wherein the X-ray generating apparatus comprises:
   a cathode unit having a plurality of emitters to emit electrons and gates to form an electric field between the gates and the emitters so that electrons are emitted from the emitters; and
   an anode unit having a target with which the electrons emitted from the cathode unit collide to generate X-rays.

7. The X-ray imaging system according to claim 6, wherein the cathode unit is formed in a flat shape, and the emitters are disposed at a surface of the flat cathode unit in a matrix.

8. The X-ray imaging system according to claim 7, wherein the target is formed in a rugged shape to prevent dispersion of X-rays.

9. The X-ray imaging system according to claim 8, wherein the target has at least one diffraction layer to diffract X-rays.

10. The X-ray imaging system according to claim 9, wherein the diffraction layer comprises at least one selected from among tungsten (W), molybdenum (Mo), lead (Pb) and platinum (Pt).

11. The X-ray imaging system according to claim 1, wherein the collimator is disposed in parallel to the X-ray generating apparatus, and the collimator or the X-ray generating apparatus is disposed so as to be movable in a manner parallel to each other.

12. An X-ray imaging system comprising:
    an X-ray generating apparatus to generate and emit X-rays;
    a detector to detect the X-rays emitted from the X-ray generating apparatus; and
    at least one collimator disposed in a path between the X-ray generating apparatus and the detector to prevent dispersion of the X-rays emitted from the X-ray generating apparatus,
    wherein the collimator comprises a plurality of capillary tubes disposed in parallel to each other, and
    each of the capillary tubes has at least one diffraction layer to diffract X-rays passing therethrough,
    wherein the X-ray generating apparatus comprises:
    a cathode unit having a plurality of emitters to emit electrons and gates to form an electric field between the gates and the emitters so that electrons are emitted from the emitters; and
    an anode unit having a target with which the electrons emitted from the cathode unit collide to generate X-rays;
    wherein the target is formed in a rugged shape to prevent dispersion of X-rays;
    wherein the target has at least one diffraction layer to diffract X-rays;
    wherein the target comprises at least one transmission layer to transmit the X-rays diffracted by the diffraction layer, and
    the diffraction layer and the transmission layer are alternately disposed to form a rugged layered structure.

13. The X-ray imaging system according to claim 12, wherein the transmission layer comprises at least one selected from among carbon (C), silicon (Si), aluminum (Al), polymer, nitride and oxide.

14. The X-ray imaging system according to claim 13, wherein the emitters are individually controllable.

15. An X-ray imaging system comprising:
    an X-ray generating apparatus to generate X-rays;
    a detector to detect the X-rays emitted from the X-ray generating apparatus and transmitted through a subject to be tested; and
    at least one collimator to collimate the X-rays emitted from the X-ray generating apparatus, wherein
    the collimator is disposed between the X-ray generating apparatus and the subject or between the subject and the detector,
    wherein the collimator comprises a plurality of capillary tubes each having a longitudinal axis disposed in parallel to each other and an advancing direction of the x-rays, and
    each of the capillary tubes has at least one diffraction layer to diffract X-rays passing therethrough.

16. The X-ray imaging system according to claim 15, wherein
    each of the capillary tubes comprises:
    at least one diffraction layer to diffract X-rays passing therethrough; and
    at least one transmission layer to transmit the X-rays diffracted by the diffraction layer,
    the diffraction layer and the transmission layer being alternately disposed from an outside of each of the capillary tubes toward a center of each of the capillary tubes to form a layered structure.

17. The X-ray imaging system according to claim 16, wherein the capillary tubes include a plurality of diffraction layers, and distances between the diffraction layers are equal to each other.

18. The X-ray imaging system according to claim 15, wherein the collimator comprises a plurality of crystal lattices to filter X-rays which have a specific wavelength.

19. The X-ray imaging system according to claim 15, wherein the collimator is disposed in parallel to the X-ray generating apparatus, and the collimator or the X-ray generating apparatus is disposed so as to be movable in a direction parallel to each other.

20. The X-ray imaging system according to claim 15, wherein the X-ray generating apparatus comprises:
   a cathode unit having a plurality of emitters to emit electrons and gates to form an electric field between the gates and the emitters so that electrons are emitted from the emitters; and
   an anode unit having a target with which the electrons emitted from the cathode unit collide to generate X-rays.

21. The X-ray imaging system according to claim 20, wherein the target comprises a plurality of layers made of different materials.

22. The X-ray imaging system according to claim 21, wherein
   the layers comprise at least one diffraction layer to diffract X-rays and at least one transmission layer to transmit X-rays, and
   the diffraction layer and the transmission layer are alternately disposed to form a rugged layered structure.

* * * * *